United States Patent
Carr et al.

(10) Patent No.: US 6,465,409 B1
(45) Date of Patent: Oct. 15, 2002

(54) SYSTEM BASED ON A BIOCIDE AND ON A POLYETHER SILICON FOR DISINFECTING HARD SURFACES

(75) Inventors: John Frederic Carr, Gloucester (GB); Gérard Mignani; Louis Vovelle, both of Lyons (FR); Brian Davis, Doncaster (GB); Caroll Vergelati, Saint-Baudille de la Tour (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/509,795

(22) PCT Filed: Oct. 13, 1998

(86) PCT No.: PCT/FR98/02198

§ 371 (c)(1),
(2), (4) Date: Mar. 31, 2000

(87) PCT Pub. No.: WO99/18784

PCT Pub. Date: Apr. 22, 1999

(30) Foreign Application Priority Data

Oct. 15, 1997 (FR) .............................. 97 12887

(51) Int. Cl.$^7$ .............................. C11D 3/48; C11D 9/36
(52) U.S. Cl. ................ 510/382; 510/130; 510/131; 510/235; 510/238; 510/289; 510/286; 510/356; 510/384; 510/385; 510/386; 510/387; 510/388; 510/391; 510/504; 510/466; 510/319
(58) Field of Search ................ 510/130, 131, 510/235, 238, 289, 286, 356, 382, 384, 383, 386, 387, 388, 391, 504, 466, 319

(56) References Cited

U.S. PATENT DOCUMENTS 5,688,747 A * 11/1997 Khan et al. ................. 508/208

FOREIGN PATENT DOCUMENTS

| DE | 3436177 | 4/1986 | ........... B01F/17/54 |
| GB | 2 285 232 | 7/1995 | ......... C09D/183/12 |
| JP | 6-279268 | * 10/1994 | |

OTHER PUBLICATIONS

Database WPI, Derwent Publications Ltd., London, GB; AN 82–01144J, XP002069871 Duskin Franchise KK.

Chemical Patents Index, Documentation Abstracts Journal, Week 9306, Derwent Publications Ltd., London, GB; AN 93–049503, XP002085184, & JP 05 000905 A (Sankyo Co Ltd) Jan. 8, 1993) see abstract.

International Search Report Mar. 1995.

* cited by examiner

Primary Examiner—Charles Boyer

(57) ABSTRACT

The invention concerns an aqueous biocide system comprising: at least one water-soluble or water-dispersible biocidal agent, and at least a polyorganosiloxane with water-soluble or water-dispersible functions. The invention also concerns the use of the system for disinfecting hard surfaces, or a method for disinfecting hard surfaces using the system, with controlled release of the biocide when contacted with an aqueous medium of a hard surface whereon the aqueous medium has been deposited and dried.

11 Claims, No Drawings

SYSTEM BASED ON A BIOCIDE AND ON A POLYETHER SILICON FOR DISINFECTING HARD SURFACES

This application is an application under 35 U.S.C. Section 371 of International Application Number PCT/FR98/02198, filed on Oct. 13, 1998.

The present invention relates to an aqueous system based on a biocide and on a polyorganosiloxane containing polyether functions, as well as to its use for the long-lasting disinfection of hard surfaces by slow, gradual release of the said biocide after application, by contact with water on the treated surface.

Aqueous biocidal compositions for treating hard surfaces generally have the drawback of rapidly losing their efficacy after they have been applied, in particular when the surfaces treated are then washed.

To overcome this drawback, it has been proposed to use film-forming organic polymers in these compositions in order to form, after application, a physical barrier which prevents the biocide from being released too quickly.

It has thus been suggested (WO 97/06675 from Rhône-Poulenc Chemicals Ltd.) to combine with a biocide a terephthalic copolyester having polyoxyethylene or polyoxyethylene terephthalate units in its polymer chain.

The Applicant has found a high-performance aqueous biocidal system.

A first subject of the invention is an aqueous biocidal system comprising at least one water-soluble or water-dispersible biocidal agent, and at least one polyorganosiloxane containing water-soluble or water-dispersible polyether functions, of formula (I)

$$R^1R^2R^3SiO(R^4R^5SiO)_p(R^6QSiO)_qSiR^3R^2R^1 \quad (I)$$

in which formula the symbols $R^1$, $R^2$, $R^4$, $R^5$ and $R^6$, which may be identical or different, represent a phenyl or a $C_1$ to $C_6$ alkyl radical, preferably methyl, the symbols $R^3$, which may be identical or different, represent a phenyl or $C_1$ to $C_6$ alkyl radical, preferably methyl, or the symbol Q, the symbol Q represents a polyoxyalkylene ether residue of formula

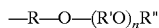

—R—O—(R'O)$_n$R'' where

R represents
a linear $C_3$ to $C_{15}$, preferably $C_3$ to $C_{10}$, alkyl group, most particularly trimethylene,
a branched $C_4$ to $C_{15}$, preferably $C_4$ to $C_{10}$, alkyl group, most particularly 2-methyltrimethylene,
the unit (R'O)$_n$ represents a poly(ethylenoxy) and/or poly(propylenoxy) group,
n is an average value ranging from 5 to 200, preferably from 5 to 100
R'' represents H or a $C_1$ to $C_6$, preferably $C_1$, alkyl group
p is an average value ranging from 10 to 200, preferably from 10 to 100
q is
a value q1 equal to 0, $R^3$ in this case representing the symbol Q or, preferably, an average value q2 ranging from 1 to 100, preferably from 5 to 50, irrespective of $R^3$.

It has been observed, advantageously, that the polyorganosiloxane structure of the polymer of formula (I) not only allows adhesion and wetting of the biocidal system to the support to be treated, but also creates a preferential interaction between the biocide and the polyether functions, by virtue of the high mobility of the polyorganosiloxane skeleton due to the low glass transition temperature of the polymer (Tg less than room temperature).

Among the biocidal agents which may be present in the said system of the invention, mention may be made of cationic, amphoteric, amino, phenolic and halogen-containing biocides. Systems based on cationic biocides are particularly advantageous.

As examples of biocides, mention may be made of:

cationic biocides such as quaternary monoammonium salts such as cocoalkylbenzyldimethylammonium, $C_{12}$–$C_{14}$alkylbenzyldimethylammonium, cocoalkyldichlorobenzyldimethylammonium, tetradecylbenzyldimethylammonium, didecyldimethylammonium and dioctyldimethylammonium chlorides myristyltrimethylammonium and cetyltrimethylammonium bromides monoquaternary heterocyclic amine salts such as laurylpyridinium, cetylpyridinium and $C_{12}$–$C_{14}$alkylbenzylimidazolium chlorides triphenylphosphonium fatty alkyl salts such as myristyltriphenylphosphonium bromide polymeric biocides such as those derived from the reaction of epichlorohydrin and of dimethylamine or diethylamine of epichlorohydrin and of imidazole of 1,3-dichloro-2-propanol and of dimethylamine of 1,3-dichloro-2-propanol and of 1,3-bis(dimethylamino)-2-propanol of ethylene dichloride and of 1,3-bis(dimethylamino)-2-propanol of bis(2-chloroethyl)ether and of N,N'-bis(dimethylaminopropyl)urea or -thiourea biguanidine polymer hydrochlorides, such as Vantocil IB amphoteric biocides such as derivatives of N-(N'-$C_8$-$C_{18}$alkyl-3-aminopropyl)glycine, of N—(N'—(N"—$C_8$-$C_{18}$alkyl-2-aminoethyl)-2-aminoethyl)glycine, of N,N-bis(N'—$C_8$-$C_{18}$-alkyl-2-aminoethyl)glycine, such as (dodecyl) (aminopropyl) glycine and (dodecyl) (diethylenediamine) glycine amines such as N-(3-aminopropyl)-N-dodecyl-1,3-propanediamine phenolic biocides such as para-chloro-meta-xylenol, dichloro-meta-xylenol, phenol, cresols, resorcinol, resorcinol monoacetate, and their derivatives or water-soluble salts halogenated biocides such as iodophores and hypochlorite salts, such as sodium dichloroisocyanurate Among the polyorganosiloxanes containing polyether functions which can be used in the system of the invention, mention may be made most particularly of those of formulae

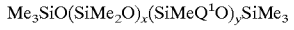

$$Me_3SiO(SiMe_2O)_x(SiMeQ^1O)_ySiMe_3$$

and

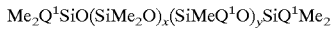

$$Me_2Q^1SiO(SiMe_2O)_x(SiMeQ^1O)_ySiQ^1Me_2$$

in which formulae x is an average value ranging from 10 to 200, preferably from 10 to 100, y is an average value ranging from 1 to 100, preferably from 5 to 50

$Q^1$ represents the radical

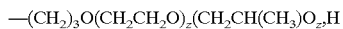

or

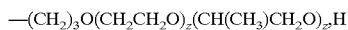

z is an average value ranging from 5 to 200, preferably from 5 to 100 z' is an average value ranging from 0 to 100, preferably from 0 to 50 with z and z'ranging from 5 to 200, preferably from 5 to 100.

The biocidal agent and the polyorganosiloxane containing polyether functions represent the main constituents of the aqueous biocidal system forming the subject of the invention.

The biocide is preferably present in the aqueous biocidal system at a concentration of about 0.1% to 20% by weight, preferably of about 0.5% to 5% by weight.

The polyorganosiloxane containing polyether functions of formula (I) is preferably present in the aqueous biocidal system at a concentration of about 0.01% to 20% by weight, preferably of about 0.05 to 5% by weight.

The relative amounts of biocide and of polyorganosiloxane containing polyether functions can correspond to a biocide/polyorganosiloxane containing ether functionality weight ratio of about 0.1 to 50, preferably of about 0.5 to 25.

A first specific embodiment of the invention consists of an aqueous biocidal system in the form of an aqueous solution, in which system the biocidal agent and the polyorganosiloxane containing polyether functions are water-soluble.

According to the invention, along with the biocide and the polyorganosiloxane containing polyether functions, the main constituents of the aqueous biocidal system of the invention, other constituents, such as surfactants, chelating agents (such as aminocarboxylates, (ethylenediaminetetra-acetates, nitrilotriacetates, N,N-bis(carboxymethyl)-glutamates, citrates), alcohols (ethanol, isopropanol, glycols), detergency adjuvants (phosphates, silicates), dyes, fragrances, etc., may advantageously be present.

A second specific embodiment of the invention consists of a biocidal system containing, besides the biocide and the polyorganosiloxane containing polyether functions, at least one surfactant, particularly a nonionic, amphoteric, zwitterionic or anionic surfactant; these may be present in a proportion of from 1 to 25%, preferably from about 2 to 10%, of the weight of the said aqueous biocidal system.

Among the surfactants which may be present, mention may be made in particular of:

nonionic surfactants such as ethylene oxide/propylene oxide block polymers, polyethoxylated sorbitan esters, fatty esters of sorbitan, ethoxylated fatty esters (containing from 1 to 25 units of ethylene oxide), polyethoxylated $C_8$–$C_{22}$ alcohols (containing from 1 to 25 units of ethylene oxide), polyethoxylated $C_6$–$C_{22}$ alkylphenols (containing from 5 to 25 units of ethylene oxide), alkylpolyglycosides, amine oxides (such as $C_{10}$–$C_{18}$alkyldimethylamine oxides, $C_8$–$C_{22}$alkoxyethyldihydroxyethylamine oxides)

amphoteric or zwitterionic surfactants such as $C_6$–$C_{20}$alkylamphoacetates or amphodiacetates (such as cocoamphoacetates), $C_{10}$–$C_{18}$alkyldimethylbetaines, $C_{10}$–$C_{18}$-alkylamidopropyldimethylbetaines, $C_{10}$–$C_{18}$alkyldimethylsulphobetaines, $C_{10}$–$C_{18}$alkylamidopropyldimethylsulphobetaines.

One preferred form of this second specific embodiment consists of an aqueous biocidal system comprising:

at least one cationic, amphoteric or amino biocide, preferably a cationic biocide, at least one polyorganosiloxane containing polyether functions, of formula (I), and at least one nonionic, amphoteric or zwitterionic surfactant, preferably a nonionic surfactant.

Most preferably, the said system is in the form of an aqueous solution.

A second subject of the invention consists in using the biocidal system as described above for the disinfection of hard surfaces, or in a process for the disinfection of hard surfaces by using the said system.

The said system may be used to disinfect floors, walls, work surfaces, equipment, furniture, instruments, etc., in industry, in the agrifoods sector, in the domestic sectors (kitchens, bathrooms, etc.) and in combination.

Among the surfaces which can be treated, mention may be made of those made of ceramic, glass, polyvinyl chloride, formica or other hard organic polymer, stainless steel, aluminium, wood, etc.

The disinfection operation consists in applying the said biocidal system, which may have been diluted 1- to 1000-fold, preferably 1- to 100-fold, to the hard surface to be treated.

The amount of biocidal system which can favourably be used is that corresponding to an application of 0.01 to 10 g, preferably of 0.1 to 1 g, of biocide per m² of surface and to an application of from 0.001 to 2 g, preferably from 0.01 to 0.5 g, of polyorganosiloxane containing polyether functions per m² of surface.

After applying and drying the aqueous biocidal system on the hard surface, the biocidal agent in the system acts by controlled release when the treated surface is made wet with water or with aqueous soiling. This availability of the biocidal agent is limited to the volume of water or of aqueous medium in contact with it.

The biocidal system has the advantage of remaining active after the surface on which it has been applied has been washed a large number of times.

A third subject of the invention consists of the use, in an aqueous biocidal system for disinfecting a hard surface comprising-at least one water-soluble or water-dispersible biocidal agent, of at least one polyorganosiloxane containing water-soluble or water-dispersible polyether functions, of formula (I) above, as an agent for interacting with the said biocide for the controlled release of this biocide during contact with an aqueous medium (water or an aqueous soiling material, in particular) of the said hard surface onto which the said aqueous system has been applied and dried.

A final subject of the invention consists of a process for disinfecting a hard surface by controlled release of at least one water-soluble or water-dispersible biocidal agent during contact with an aqueous medium (water or an aqueous soiling material, in particular) of the said hard surface onto which an aqueous system has previously been applied and dried, this aqueous system comprising at least one water-soluble or water-dispersible biocidal agent and at least one polyorganosiloxane containing water-soluble or water-dispersible polyether functions, of formula (I) above, which interact with the said biocidal agent.

Among the microorganisms whose proliferation can be controlled using the biocidal system of the invention, mention may be made of Gram-negative bacteria such as: *Pseudomonas aeruginosa; Escherichia coli; Proteus mirabilis*

Gram-positive bacteria such as: *Staphylococcus aureus; Streptococcus faecium* other dangerous bacteria in food, such as: *Salmonella typhimurium; Listeria monocytogenes; Campylobacter jejuni; Yersinia enterocolitica* yeasts such as: *Saccharomyces cerevisiae; Candida albicans* fungi such as: *Aspergillus niger; Fusarium solani; Penicillium chrysogenum* algae such as: *Chlorella saccharophilia; Chlorella emersonii; Chlorella vulgaris; Chlamydomonas eugametos*

The biocidal system of the invention is most particularly effective on the Gram-negative microorganism *Pseudomonas aeruginosa*, the Gram-positive microorganism *Staphylococcus aureus*, and the fungus *Aspergillus niger*.

The examples which follow are given by way of illustration.

EXAMPLE 1

Biocidal Activity—Interaction—

The following are prepared a biocidal solution A consisting of Rhodaquat RP 50 (aqueous solution containing 50% active material of $C_{12}$–$C_{14}$alkylbenzyldimethylammonium chloride, marketed by Rhône-Poulenc) and water and aqueous biocidal systems B, C and D, consisting of aqueous solutions of Rhodaquat RP 50 and polyether silicone of formula

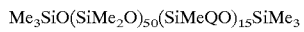

where Q represents the —$(CH_2)_3O(CH_2CH_2O)_{11}H$ radical whose concentrations are given in Table 1.

The biocidal activity of this solution and of these systems is measured according to the standard suspension test BS: 6471, under the following conditions

| | |
|---|---|
| diluent | hard water (200 ppm) |
| test strain | *Escherichia coli* ATCC 11229 |
| temperature | 22° C. |
| contact time | 10 minutes |
| interfering substance | sterile horse serum (5%) |
| neutralizing agent | polysorbate Tween 80 (3%) + soybean lecithin (2%) |
| RESULTS | dilution corresponding to a $\log_{10}$ value, of reduction in the number of viable bacterial cells, of 4 |

TABLE 1

| Composition | Biocidal solution or system | | | |
| --- | --- | --- | --- | --- |
| | A | B | C | D |
| Rhodaquat RP 50 (solution containing 50% by weight of active material) | 3% | 3% | 3% | 3% |
| Polyether silicone | — | 1.5% | 3% | 6% |
| Water | qs 100% | qs 100% | qs 100% | qs 100% |
| Result Number of dilutions | 75x | 75x | 75x | 50x |

It is observed that when the polyether silicone/biocidal active material weight ratio is 4/1, the biocidal agent is partially deactivated, on account of the interaction of the biocide molecules with the polyether silicone.

EXAMPLES 2 TO 5

Test of Disinfection of a Hard Surface

1) Biocidal Aqueous Solutions Tested

The following biocidal aqueous solutions i) and ii) are prepared

| | | |
|---|---|---|
| i) | solution of Rhodaquat RP 50 | 3% (i.e. 1.5% of biocidal active material) - Example 2 |
| ii) | solution consisting of: | 3% (i.e. 1.5% of biocidal active material) |
| | Rhodaquat RP 50 | |
| | + nonionic surfactant | 5% ($C_{10}$ alcohol containing 6 ethylene oxide units) |
| | + polyether silicone | 3%, 0.75% and 0.15% - Examples 3, 4 and 5 respectively |

These solutions are then diluted 60-fold in order to carry out the test.

2) Embodiment of the Test on a White Ceramic Tile

1. Add 3 g of dilute biocidal aqueous solution to the surface of the ceramic tile (5 cm×5 cm) which has been presterilized by cleaning with isopropyl alcohol. Dry at 45° C. in an oven.
2. Place the surface of the tile vertically and spray it with one gram of water using a hand-sprayer. This corresponds to washing without any mechanical action. Several washes are carried out before drying at 45° C.
3. Add 0.25 ml of an aqueous medium containing about $10^8$ CFU/ml of Gram-negative bacteria, *Pseudomonas aeruginosa*, spread over the pretreated hard surface.
4. Leave at room temperature for 3 hours, in order to allow the biocide to migrate from the surface of the polymer and kill the bacteria at the surface.
5. Dry at 37° C. for at least 30 minutes.
6. Recover the surviving microorganisms using a sterile pad of cotton wool which has been premoistened with a neutralizing solution. Clean the entire surface thoroughly by wiping 4 times in all directions.
7. Introduce the pad into 9 ml of neutralizing medium; adjust the volume to 10 ml with water. Transfer the bacterial suspension onto nutrient agar in Petri dishes by successive dilutions of a factor of 10.
8. Incubate the dishes at 37° C. for 48 hours and count the surviving microorganisms.

The neutralizing medium contains 3% of polysorbate Tween 80 and 2% of soybean lecithin.

A control test is carried out by performing steps 1. to 7. on the surface of a white ceramic tile (5 cm×5 cm) which has been presterilized but not treated with the biocidal system.

The $\log_{10}$ value of reduction in the number of bacteria is calculated as follows:

$$\log_{10} \text{ of reduction} = \log_{10} N/n$$

N being the number of surviving bacteria (as CFU/ml) in the control test n being the number of surviving bacteria (as CFU/ml) in the test using the biocidal system 3) Results The results of the above test performed with solutions i) and ii) are featured in Tables 2 and 3.

The results of Example 2 show that an aqueous solution of biocidal agent alone withstands up to two washes, considering a $\log_{10}$ value of reduction of 3 as sufficient for the general disinfection of a surface.

The results of Example 3 show that the interaction between the biocide and the polyether silicone reduces the efficacy of the biocide in attacking the bacteria. The effective biocidal activity lasts, however, for 4 washes. Slow release of the biocide is observed.

The results of Example 4 show that a weaker interaction between the biocide and polyether silicone, by reducing the amount of polyether silicone present in the system, allows more biocide to be released for the initial attack on the bacteria. The effective biocidal activity lasts for at least 16 washes.

The results of Example 5 show that if this interaction is decreased further, the amount of biocide released for attack on the bacteria is even larger. In this case, a higher initial biocidal activity and a more effective biocidal activity for at least 8 washes are observed.

EXAMPLE 6

Example 5 is repeated using the following polymer as polyether silicone:

$$Me_3SiO(SiMe_2O)_{75}(SiMeQO)_7SiMe_3$$

in which Q represents the radical $-(CH_2)_3O(R'O)_nH$, the group $(R'O)_n$ of which comprises on average 22 oxyethylene units and 23.5 oxypropylene units.

The results obtained are given in Table 4.

TABLE 2

|  | Composition (active material) | Amount applied to the surface (g/m²) | | | |
| --- | --- | --- | --- | --- | --- |
| Example 2 |  |  | | | |
| polyether silicone | 0 | 0 | | | |
| biocide | 1.5 | 0.3 | | | |
| nonionic surfactant | 0 | 0 | | | |
| number of washes | 0 | 1 | 2 | 4 | 8 | 16 |
| $\log_{10}$ of reduction | 6.0 | 5.9 | 3.6 | 1.2 | 0.1 | |
| Example 3 |  |  | | | |
| polyether silicone | 3 | 0.6 | | | |
| biocide | 1.5 | 0.3 | | | |
| nonionic surfactant | 5 | 1.0 | | | |
|  |  | total = 1.9 | | | |
| number of washes | 0 | 1 | 2 | 4 | 8 | 16 |
| $\log_{10}$ of reduction | 3.47 | 3.24 | 3.0 | 3.14 | 2.03 | 2.02 |

TABLE 3

|  | Composition (active material) | Amount applied to the surface (g/m²) | | | |
| --- | --- | --- | --- | --- | --- |
| Example 4 |  |  | | | |
| polyether silicone | 0.75 | 0.15 | | | |
| biocide | 1.5 | 0.3 | | | |
| nonionic surfactant | 5 | 1.0 | | | |
|  |  | total = 1.45 | | | |
| number of washes | 0 | 1 | 2 | 4 | 8 | 16 |
| $\log_{10}$ of reduction | 4.32 |  | 3.10 | 3.24 | 3.17 | 3.25 |
| Example 5 |  |  | | | |
| polyether silicone | 0.15 | 0.03 | | | |
| biocide | 1.5 | 0.3 | | | |
| nonionic surfactant | 5 | 1.0 | | | |
|  |  | total = 1.33 | | | |
| number of washes | 0 | 1 | 2 | 4 | 8 | 16 |
| $\log_{10}$ of reduction | 4.78 |  | 3.79 | 3.63 | 3.78 | |

TABLE 4

|  | Composition (active material) | Amount applied to the surface (g/m²) | | | |
| --- | --- | --- | --- | --- | --- |
| Example 6 |  |  | | | |
| polyether silicone | 0.15 | 0.03 | | | |
| biocide | 1.5 | 0.3 | | | |
| nonionic surfactant | 5 | 1.0 | | | |
|  |  | total = 1.33 | | | |
| number of washes | 0 | 1 | 2 | 4 | 8 | 16 |
| $\log_{10}$ of reduction | 4.14 |  | 4.10 | 4.17 | 3.56 | 3.57 |

What is claimed is:

1. A process for disinfecting a hard surface by controlled release of at least one water-soluble or water-dispersible biocidal agent, comprising the steps of applying an aqueous biocidal system onto a hard surface, drying the applied aqueous biocidal system, and then contacting the dried biocidal system with an aqueous medium, such that the biocidal agent is released, said aqueous biocidal system comprising at least one water-soluble or water-dispersible biocidal agent and at least one polyorganosiloxane containing water-soluble or water-dispersible polyether functions, of formula (I)

$$R^1R^2R^3SiO(R^4R^5SiO)_p(R^6QSiO)_qSiR^3R^2R^1 \quad (I)$$

wherein the symbols $R^1$, $R^2$, $R^4$, $R^5$ and $R^6$, which are identical or different, represent a phenyl or a $C_1$ to $C_6$ alkyl radical, the symbols $R^3$, which are identical or different, represent a phenyl, a $C_1$ to $C_6$ alkyl radical, or the symbol Q, the symbol Q represents a polyoxyalkylene ether residue of formula:

$$-R-O-(R'O)_nR''$$

wherein: R represents a linear $C_3$ to $C_{15}$, alkylene group, or a branched $C_4$ to $C_{15}$ alkylene group, the unit $(R'O)_n$ represents a poly(ethylenoxy) or poly(propylenoxy) group, n is an average value ranging from 5 to 200, and R" represents H or a $C_1$ to $C_6$ alkyl group, p is an average value ranging from 10 to 200, and q is a value q1 equal to 0, $R^3$ in this case representing the symbol Q, or an average value q2 ranging from 1 to 100, irrespective of $R^3$, and which interact with said biocidal agent.

2. A process according to claim 1, wherein said biocidal agent is a cationic, amphoteric, amino, phenolic or halo biocidal agent.

3. A process according to claim 1, wherein the polyorganosiloxane containing polyether functions has the formula:

$$Me_3SiO(SiMe_2O)_x(SiMeQ^1O)_ySiMe_3$$

or $$Me_2Q^1SiO(SiMe_2O)_x(SiMeQ^1O)_ySiQ^1Me_2$$

wherein:

x is an average value ranging from 10 to 200, y is an average value ranging from 1 to 100, $Q^1$ represents the radical:

$$-(CH_2)_3O(CH_2CH_2O)_z(CH_2CH(CH_3)O)_{z'}H$$

z is an average value ranging from 5 to 200, and z' is an average value ranging from 0 to 100, with z+z' ranging from 5 to 200.

4. A process according to claim 3, wherein the system is in the form of an aqueous solution and wherein the biocidal agent and polyorganosiloxane containing polyether functions are water-soluble.

5. A process according to claim 1, wherein the biocidal agent is present in the aqueous biocidal system at a concentration of about 0.1% to 20% by weight.

6. A process according to claim 3, wherein the polyorganosiloxane containing polyether functions of formula (I) is present in the aqueous biocidal system at a concentration of about 0.01% to 20% by weight.

7. A process according to claim 1, wherein the relative amounts of biocidal agent and of polyorganosiloxane containing ether functions correspond to a biocidal agent/polyorganosiloxane containing ether functionality weight ratio of about 0.1 to 50.

8. A process according to claim 1, wherein said aqueous biocidal system further comprises at least one other constituent, said constituent being a surfactant.

9. A process according to claim 8, wherein said aqueous biocidal system comprises at least one cationic, amphoteric or amino biocidal agent, at least one polyorganosiloxane containing polyether functions, of formula (I), and at least one nonionic, amphoteric or zwitterionic surfactant.

10. A process according to claim 8, wherein said surfactant is present in a proportion of from 1 to 25%, of the weight of said aqueous biocidal system.

11. A process according to claim 10, wherein the amount of biocidal system applied and dried corresponds to an application of 0.01 to 10 g of biocidal agent per $m^2$ of surface and to an application of 0.001 to 2 g of polyorganosiloxane containing polyether functions per $m^2$ of surface.

* * * * *